US010130657B2

(12) United States Patent
Hughes (10) Patent No.: US 10,130,657 B2
(45) Date of Patent: Nov. 20, 2018

(54) FORMULATION, APPARATUS, AND METHODS FOR TREATMENT OF BRAIN TRAUMA

(71) Applicant: John C. Hughes, Basalt, CO (US)

(72) Inventor: John C. Hughes, Basalt, CO (US)

( * ) Notice: Subject to any disclaimer, the term of this patent is extended or adjusted under 35 U.S.C. 154(b) by 0 days.

(21) Appl. No.: 15/043,573

(22) Filed: Feb. 14, 2016

(65) Prior Publication Data
US 2016/0235786 A1 Aug. 18, 2016

Related U.S. Application Data

(60) Provisional application No. 62/116,112, filed on Feb. 13, 2015.

(51) Int. Cl.
| | | |
|---|---|---|
| *A61K 33/00* | (2006.01) | |
| *A61N 2/00* | (2006.01) | |
| *A61M 11/00* | (2006.01) | |
| *A61K 45/06* | (2006.01) | |
| *A61K 35/16* | (2015.01) | |
| *A61K 9/00* | (2006.01) | |
| *A61K 35/545* | (2015.01) | |
| *A61K 31/714* | (2006.01) | |
| *A61B 5/0482* | (2006.01) | |
| *A61N 5/06* | (2006.01) | |
| *A61N 5/067* | (2006.01) | |
| *A61M 15/08* | (2006.01) | |

(52) U.S. Cl.
CPC ............ *A61K 35/16* (2013.01); *A61K 9/0043* (2013.01); *A61K 31/714* (2013.01); *A61K 35/545* (2013.01); *A61B 5/0482* (2013.01); *A61M 11/007* (2014.02); *A61M 15/08* (2013.01); *A61M 2205/05* (2013.01); *A61N 2/002* (2013.01); *A61N 2/006* (2013.01); *A61N 5/06* (2013.01); *A61N 2005/067* (2013.01)

(58) Field of Classification Search
CPC .... A61K 35/16; A61K 9/0043; A61K 35/545; A61K 33/00; A61K 45/06; A61N 2/002; A61N 5/06; A61M 11/007; A61B 5/0482; A61G 10/026
USPC ........................................................ 604/514
See application file for complete search history.

(56) References Cited

U.S. PATENT DOCUMENTS

| | | | | |
|---|---|---|---|---|
| 4,880,813 A * | 11/1989 | Frost | ..................... | A61K 31/485 514/282 |
| 8,283,160 B2 † | 10/2012 | Frey, II | | |
| 8,822,492 B2 * | 9/2014 | Schachter | ............ | A61K 9/0019 424/450 |
| 2008/0292597 A1 * | 11/2008 | Steenblock | .......... | A61K 9/0019 424/93.7 |
| 2009/0012039 A1 * | 1/2009 | Kurtz | ..................... | A61K 31/714 514/52 |

OTHER PUBLICATIONS

Gasior et al. Neuroprotective and Disease-Modifying Effects of the Ketogenic Diet; Behavioral Pharmacology, vol. 17, No. 5-6 (2006) pp. 431-439.*
Harting et al. Cell Therapies for Traumatic Brain Injury; Neurosurgical Focus, vol. 24, No. 0 (2008) pp. 1-21.*
Demirtas-Tatlidede et al. Noninvasive Brain Stimulation in Traumatic Brain Injury; Journal of Head Trauma and Rehabilitation; vol. 27, No. 4 (2012) pp. 274-292.*
Wu et al. Low-Level Laser Therapy for Closed-Head Traumatic Brain Injury in Mice: Effect of Different Wavelengths; Lasers in Surgery and Medicine, vol. 44, No. 3 (2012) pp. 218-226.*
Hammond, D. Neurofeedback Treatment for Traumatic Brain Injury; International Brain Injury Association (2012) downloaded from http//:www.internationalbrain.org/articles/neurofeedback-treatment-for-traumatic-brain-injury/ on Apr. 25, 2017.*
Greenman et al. Cranial Findings and Iatrogenesis From Craniosacral Manipulation in Patients With Traumatic Brain Syndrome; The Journal of the American Osteopathic Association, vol. 95 (1995) pp. 182-192.*
Neubauer et al. Late Treatment of Severe Brain Injury With Hyperbaric Oxygenation; Journal of American Physicians and Surgeons, vol. 10, No. 2 (2005) pp. 58-59.*
Schwarzbold et al. Psychiatric Disorders and Traumatic Brain Injury; Neuropsychiatric Disease and Treatment, vol. 4, No. 4 (2008) pp. 797-816.*
Mischley et al. Safety Survey of Intranasal Glutathione; The Journal of Alternative and Complementary Medicine; vol. 19, No. 5 (2013) pp. 459-463.*
Brabazon et al. Intranasal Insulin Treatment of Traumatic Brain Injury; Journal of Neurotrauma, vol. 31, pp. A1-A126 (2014) Abstract D1-17.*
Anitua et al. Intranasal Delivery of Plasma and Platelet Growth Factors Using PRGF-Endoret System Enhances Neurogenesis in a Mouse Model of Alzheimers Disease; PLOS One, vol. 8, No. 9 (2013) pp. 1-13.*
Young et al. Effect of Parenteral Nutrition Upon Intracranial Pressure in Severe Head Injury; Journal of Neurosurgery, vol. 67 (1987) pp. 76-80.*

(Continued)

*Primary Examiner* — Scott Long
*Assistant Examiner* — Paul C Martin
(74) *Attorney, Agent, or Firm* — William C. Milks, III (57) ABSTRACT

A formulation comprising platelet rich plasma (PRP) for treatment of patients who have experienced brain injury, consisting of a mixture of human autologous plasma, D5W, glutathione, methylcobalamin, and regular insulin. The formulation is infused directly adjacent to a patient's brain through the nostrils or nares of the nasal cavity. Treatment using the formulation may be supplemented with one or more therapies including hyperbaric oxidation therapy (HBOT), cranial osteopathic therapy, intravenous (IV) nutrition, electroencephalographic (EEG) biofeedback, low level laser therapy (LLLT), transcranial magnetic stimulation (TMS), adult stem cell treatments, and a ketogenic diet and medium-chain triglyceride (MCT) oil therapy.

19 Claims, 4 Drawing Sheets

(56) References Cited

OTHER PUBLICATIONS

Anonymous. Using the LMA MAD Nasal Intranasal Mucosal Atomization Device; Teleflex (2013) downloaded from http://teleflex.com/en/usa/productAreas/ems/documents/AN_ATM_MAD-Nasal-Usage_Guide_AI_2012-1528.pdf on Aug. 25, 2017.*
L. Danielyan et al., "Intranasal delivery of cells to the brain", 10 pages, Feb. 11, 2009, European Journal of Cell Biology.†
L. Danielyan et al., "Therapeutic Efficacy of Intranasally Delivered Mesenchymal Stem Cells in a Rat Model of Parkinson Disease", 14 pages, Nov. 1, 2011, Rejuvenation Research.†

\* cited by examiner
† cited by third party

FORMULATION, APPARATUS, AND METHODS FOR TREATMENT OF BRAIN TRAUMA

CROSS-REFERENCE TO RELATED PATENT APPLICATION

This application claims the benefit of U.S. Provisional Patent Application No. 62/116,112 filed on Feb. 13, 2015, entitled FORMULATION, APPARATUS, AND METHODS FOR TREATMENT OF BRAIN TRAUMA, the disclosure of which is hereby incorporated herein in its entirety by this reference.

BACKGROUND OF THE INVENTION

1. Field of the Invention

The present invention relates to apparatus and methods for treating personal injuries and, more particularly, to formulations, devices, and techniques for treating patients who have suffered brain injury. Specifically, various examples in accordance with the present invention provide a medicinal formulation, devices, and therapeutic protocols developed to treat trauma to the brain of a patient.

2. Description of the Prior Art

Incidences of traumatic brain injury in both developed and developing countries are on the rise. The primary reasons for the increase in traumatic brain injury include growth in population and a growing number of traffic accidents and other emergencies such as natural disasters, sports injuries, falls, and assaults. Moreover, modern military conflict has led to an additional steep rise in traumatic brain injury due to blast injuries as well as direct combat-related head injuries. The burden of traumatic brain injury in the USA has been estimated to be 1.5 million cases each year, with an annual economic cost exceeding $56 billion as of 2010.

Traumatic brain injury is characterized by mechanical forces which disrupt brain tissue in addition to all of the destructive inflammatory and ischemic/hypoxic processes of other brain injuries. For example, brain trauma may occur as a result of a force impact to the head of a person. The sources of force impacts vary. Brain trauma can be caused by accidents such as a vehicular collision during which a person's head is thrust against the steering wheel or dash board or the person's head strikes the ground as a consequence of a fall from a ladder. Brain trauma can be caused intentionally such as blunt force applied to a person's head during commission of a criminal assault or during military combat. Brain trauma may also result from any cause that results in acute loss of blood or oxygen to the brain causing brain tissue damage.

Various techniques for the treatment of traumatic brain injury are known. The various techniques include the following.

Hyperbaric oxidation therapy (HBOT) is a known treatment which enhances the body's natural healing process by inhalation of 100% oxygen in a total body chamber, where atmospheric pressure is increased and controlled. HBOT is used for a wide variety of treatments usually as a part of an overall medical care plan. Under normal circumstances, oxygen is transported throughout the body only by red blood cells. With HBOT, oxygen is dissolved into all of the body's fluids, the plasma, the central nervous system fluids, the lymph, and the bone and can be carried to areas where circulation is diminished or blocked. In this way, extra oxygen can reach all of the damaged tissues, and the body can support its own healing process. The increased oxygen greatly enhances the ability of white blood cells to kill bacteria, reduces swelling, and allows new blood vessels to grow more rapidly into the affected areas. It is a simple, non-invasive, and painless treatment. When cells in the brain die, either from trauma or lack of oxygen, blood plasma leaks out into surrounding brain tissue causing swelling and reducing blood flow. These otherwise normal cells go dormant because they cannot function without the appropriate amount of oxygen. HBOT dramatically increases the oxygen carried in the blood plasma, making oxygen available to heal damaged capillary walls, preventing plasma leakage, and reducing swelling. As the swelling decreases, blood flow can be restored to the dormant tissue (neovascularization), and these cells then have the potential to function again.

An additional known treatment for traumatic brain injury is intravenous (IV) nutrition therapy. Brain trauma triggers hypermetabolic and catabolic states, severely impairing nitrogen homeostasis. Brain trauma is characterized by disproportional pro-inflammatory cytokine (e.g., tumor necrosis factor-$\alpha$, interleukin-1, and interleukin-6) production and release that is associated with increased counter-regulatory hormones (e.g., cortisol, glucagon, and catecholamines) release. This process leads to increased systemic and cerebral energy needs, even in paralyzed patients. The increased energy needs can persist for long periods. Nutrition therapy should start early: within 24 to 48 hours of admission to an intensive care unit. The feeding should be adjusted based on the patient's nutritional requirements over the next 48 to 72 hours. This process is often challenging in severe brain trauma patients. The Brain Trauma Foundation recommends that total nutritional support should be achieved within seven days of the injury. Installing enteral access and starting enteral nutrition should be attempted as soon as volume resuscitation is complete and the patient is hemodynamically stable. Early nutritional support is able to reduce the secretion of catabolic hormones, which is already increased in this setting. IV nutrition therapy is also able to at least partially preserve the previous nutritional conditions of the patient thereby partially preserving body weight and muscle mass. Additionally, IV nutrition therapy results in less intestinal bacterial proliferation and therefore less translocation.

It is also known to treat brain trauma patients using electroencephalographic (EEG) biofeedback therapy. EEG biofeedback is a methodology for harmonizing aberrant or overactive brainwave patterns such that patients can learn to redevelop the most appropriate brainwave pattern for each environmental or social situation. Clinical evidence has shown the effectiveness of EEG biofeedback training as an adjunct modality for remediating the symptoms of minor closed head injury. For example, the Neurofeedback Wellness Center located in The Woodlands, Tex. has reported that biofeedback training appears to be effective even years post-injury, when spontaneous remediation is no longer expected.

Another known traumatic brain injury treatment is cranial osteopathic therapy. Cranial osteopathy (also called cranial therapy or craniosacral therapy) is one variety of osteopathic manipulative therapies. Cranial osteopathy stimulates healing by using gentle hand pressure to manipulate the skeleton and connective tissues, especially the skull and sacrum (the large, triangular bone at the base of the spinal column). Cranial osteopathy is based on the espoused theory that the central nervous system, including the brain and spinal cord, has subtle, rhythmic pulsations that are vital to health and can be detected and modified by a skilled practitioner.

Low level laser (light) therapy (LLLT) has been clinically applied for a wide range of medical indications requiring protection from cell and tissue death, stimulation of healing, and repair of injuries, as well as reduction of pain, swelling, and inflammation, and has been investigated in connection with the treatment of traumatic brain injury. Evidence is suggesting that red or near-infra-red light (at wavelengths that can penetrate tissue) is absorbed by mitochondrial chromophores leading to increased cellular respiration, more adenosine triphosphate (ATP) synthesis, modulation of oxidative stress, and nitric oxide production that together lead to activation of signaling pathways and gene transcription.

Transcranial magnetic stimulation (TMS) and in particular repetitive TMS (rTMS) is also known to have been used for treatment of traumatic brain injury. TMS is a painless method to stimulate the human brain. Repeated applications of TMS can influence brain plasticity and cortical reorganization through stimulation-induced alterations in neuronal excitability.

Another known therapy for brain trauma is adult stem cell therapy. Stem cells are undifferentiated, or blank, cells with the potential to give rise to many different cell types that carry out different functions. While the stem cells in adult bone marrow or umbilical cord blood tend to develop into the cells that make up the organ system from which they originated, these multipotent stem cells can be manipulated to take on the characteristics of neural cells. To date, there have been two widely-held views on how stem cells may work to provide potential treatments for brain damage caused by injury or neurodegenerative disorders. One school of thought is that stem cells implanted into the brain directly replace dead or dying cells. The other, more recent view is that transplanted stem cells secrete growth factors that indirectly rescue the injured tissue. A University of Florida study conducted in 2013 concluded that the transplanted stem cells create a neurovascular matrix that bridges the long-distance gap between the region in the brain where host neural stem cells arise and the site of injury. This pathway, or "biobridge," ferries the newly emerging host cells to the specific place in the brain in need of repair, helping promote functional recovery from traumatic brain injury.

Additionally, it is known that platelets are specialized blood cells that play a critical role in clot formation and injury healing. They are naturally extremely rich in connective tissue growth factors. Activating and injecting these growth factors into damaged ligaments, tendons, and joints ignites a person's body's own stem cells and stimulates the natural repair process.

Platelet rich plasma (PRP) has also been reported to be combined with stem cells that may be mobilized from a patient's bone marrow using the FDA approved drug Neupogen® which prods the marrow to produce replacement stem cells that tend to be more robust than those that were mobilized. The "revitalized" bone marrow (BMAC) may then be harvested and infused by intravenous injection or other means. In addition, growth factor rich PRP from a patient's own blood may be mixed with the BMAC prior to infusion. The growth factors activate stem cells and enhance their activity. The stem cells may be directed to target tissues by the use of special factors that are extracted from a patient's own blood which are injected into those areas (such as joints) where the stem cells need to go in order to effect repair and restoration. One of these factors is SDF-1 which can bring 50 times more stem cells to the injured organ or tissue than is otherwise possible. However, the use of PRP for the treatment of brain trauma, whether or not combined with a patient's own stem cells, has not heretofore been known.

A ketogenic diet and medium-chain triglyceride (MCT) oil have been used with autistic and epileptic children. Moreover, there is evidence from uncontrolled clinical trials and studies in animal models that a ketogenic diet can provide symptomatic and disease-modifying activity in a broad range of neurodegenerative disorders including Alzheimer's disease and Parkinson's disease, and may also be protective in instances of traumatic brain injury and stroke. A ketogenic diet is a high fat, adequate protein, low carbohydrate diet. MCT oil, for example, Bulletproof® Brain Octane oil, contains the most ketogenic MCT in coconut oil, C8, from the heart of the coconut. One aspect of the hypothesis for treatment using a ketogenic diet and MCT oil is an associated modification of the tricarboxylic acid cycle to increase the synthesis of the neurotransmitter gammaaminobutyric acid (GABA), leading to neuronal hyperpolarization and less of the neuroxcitatory glutamate. A ketogenic diet and MCT oil provide improved protection from oxidative stress and increased synthesis of calming neurotransmitters (including GABA).

The present invention addresses treatment of brain injury with a novel formulation, apparatus, and methods of treatment. The various examples of the present invention have been demonstrated to provide efficacious treatment of brain injury.

SUMMARY OF THE INVENTION

In accordance with various non-limiting examples of the present invention, treatment of brain injury comprises a protocol that may include various therapies. The particular therapies are selected to provide optimal recovery of a patient suffering from sub-acute to chronic symptoms related to brain injury.

Considered in more detail, in accordance with a non-limiting example of the present invention, platelet rich plasma (PRP) infusion therapy is administered by a qualified physician to a patient who has experienced brain injury. In accordance with a non-limiting example of the present invention, the PRP infusion comprises a form of blood plasma that is rich in growth factors, cytokines, and stem cell precursors. The PRP infusion further preferably comprises the plasma combined with drugs and nutrients. Although the PRP infusion in accordance with non-limiting examples of the present invention preferably comprises a combination of nutrients, the combination of nutrients is not limited to particular nutrients or combinations of nutrients, and nutrients may be added as needed, or different ratios of the same nutrients may comprise the PRP infusion, as long as the PRP remains a plasma-based cocktail. The PRP infusion is infused directly adjacent to the brain through the nostrils or nares of the nasal cavity. Additionally, a formulation delivery apparatus is provided for delivering the PRP infusion. In accordance with a non-limiting example, the patient may be treated using PRP infusion therapy at the initial consultation and then every three weeks for a total of three treatments over six weeks. Preferably, the PRP infusion therapy is then continued every four months for the following year.

In accordance with an additional non-limiting example of the present invention, a regimen of one or more treatments using hyperbaric oxidation therapy (HBOT) is administered by a qualified physician to a patient who has experienced traumatic brain injury. During the period of administration of the HBOT treatments, the patient is also treated using PRP infusion one or more times. Additionally, following each treatment of PRP infusion, cranial osteopathic therapy is performed on the patient.

In accordance with a further non-limiting example of the present invention, a regimen of 40 treatments using hyperbaric oxidation therapy (HBOT) is administered by a qualified physician to a patient, who has experienced traumatic brain injury, over a period of six weeks. During the six-week period of administration of the HBOT treatments, the patient is treated using PRP infusion at the time of the first HBOT treatment, at three weeks, and also at six weeks. Following each treatment using PRP infusion initially and again at three and six weeks, cranial osteopathic therapy is performed on the patient.

In accordance with another non-limiting example of the present invention, a regimen of 40 initial treatments using hyperbaric oxidation therapy (HBOT) administered by a qualified physician to a patient, who has experienced traumatic brain injury, over a period of six weeks is supplemented by two follow-up regimens of 20 treatments using HBOT at three and nine months from the initial HBOT regimen. The patient is treated using supplemental PRP infusions at four-month intervals for a year from the time that the initial HBOT treatment is administered. Following each supplemental treatment using PRP infusion initially and again at four-month intervals for a year from the time that the initial HBOT treatment is administered, cranial osteopathic therapy is performed on the patient.

In accordance with additional non-limiting examples of the present invention, PRP infusion, HBOT, and cranial osteopathic therapy are further supplemented with additional therapies. The additional supplemental therapies may include one or more of the following therapies: intravenous (IV) nutrition, electroencephalographic (EEG) biofeedback, low level laser therapy (LLLT), transcranial magnetic stimulation (TMS), and adult stem cell treatments.

In accordance with the various examples of the present invention, treatment of brain injury using PRP infusion has demonstrated efficacy in the treatment of brain injury. The therapeutic effects can also be enhanced when coordinated with other treatments.

The time periods between administrations of the various treatments and the durations of treatments comprising protocols in accordance with the non-limiting examples of the present invention are examples only and are not limited to particular frequencies or lengths of time that particular treatments are administered. Furthermore, the administration of treatments comprising a protocol in accordance with the non-limiting examples of the present invention are examples only and are not limited to a particular sequence.

The foregoing and other objects, features, and advantages of the present invention will become more readily apparent from the following detailed description of various examples of the present invention, which proceeds with reference to the accompanying drawing.

BRIEF DESCRIPTION OF THE DRAWING

The various examples of the present invention will be described in conjunction with the accompanying figures of the drawing to facilitate an understanding of the present invention. In the figures, like reference numerals refer to like elements. In the drawing.

DETAILED DESCRIPTION OF THE PREFERRED EXAMPLE EMBODIMENTS

In accordance with one non-limiting example of the present invention, a protocol is provided to repair injured brain tissue in patients suffering from sub-acute to chronic symptoms related to traumatic brain injury. The traumatic brain injury protocol consists of one or more therapies. The traumatic brain injury protocol has been proven to aid in the recovery of patients who have suffered traumatic brain trauma caused by automobile injury, blunt trauma injury, military injury, or sports injury, for example.

In accordance with a non-limiting example of the present invention, a formulation comprising platelet rich plasma (PRP) is used in the treatment of patients who have experienced traumatic brain injury. The PRP is a specialized form of blood plasma that is rich in growth factors, cytokines, and stem cell precursors.

The formulation in accordance with one non-limiting example of the present invention also comprises drugs and nutrients for treatment of traumatic brain injury. In accordance with one example embodiment, the formulation consists of a mixture of approximately 75% by volume human autologous plasma, 15% by volume D5W, 5% by volume glutathione, 4% by volume methylcobalamin, and less than 1% by volume regular insulin. The foregoing volumetric percentages are approximate percentages in that the percentages have a range of plus or minus 1%.

After the above-described formulation is prepared, in accordance with a non-limiting example of the present invention, the formulation is infused slowly into the frontal region of the brain of a patient suffering from traumatic brain injury. In accordance with one non-limiting example, the formulation is delivered directly adjacent to the brain through the nostrils or nares of the nasal cavity as will now be described.

Figure 1:
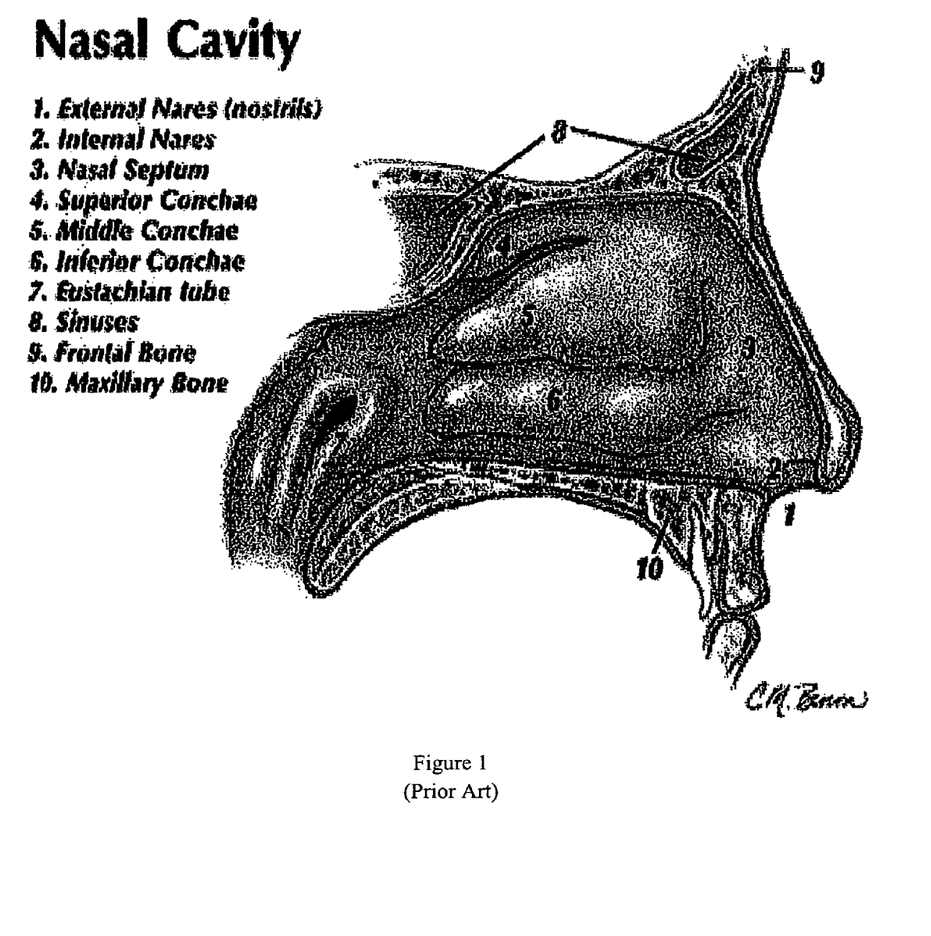
FIG. 1 illustrates the anatomy of a nostril (or naris) which is one of the two channels of the nose, from the point where they bifurcate to the external opening.

FIG. 1 illustrates the anatomy of a nasal cavity including a nostril (or naris) which is one of the two channels of the nose, from the point where they bifurcate to the external opening indicated by the numeral 1. The internal naris is indicated by the numeral 2. The septum 3 that divides the nose into two nares is indicated by the numeral 3. The internal tissue of the nasal cavity comprises superior conchae, middle conchae, and inferior conchae indicated by the numerals 4, 5, and 6, respectively.

Figure 2:
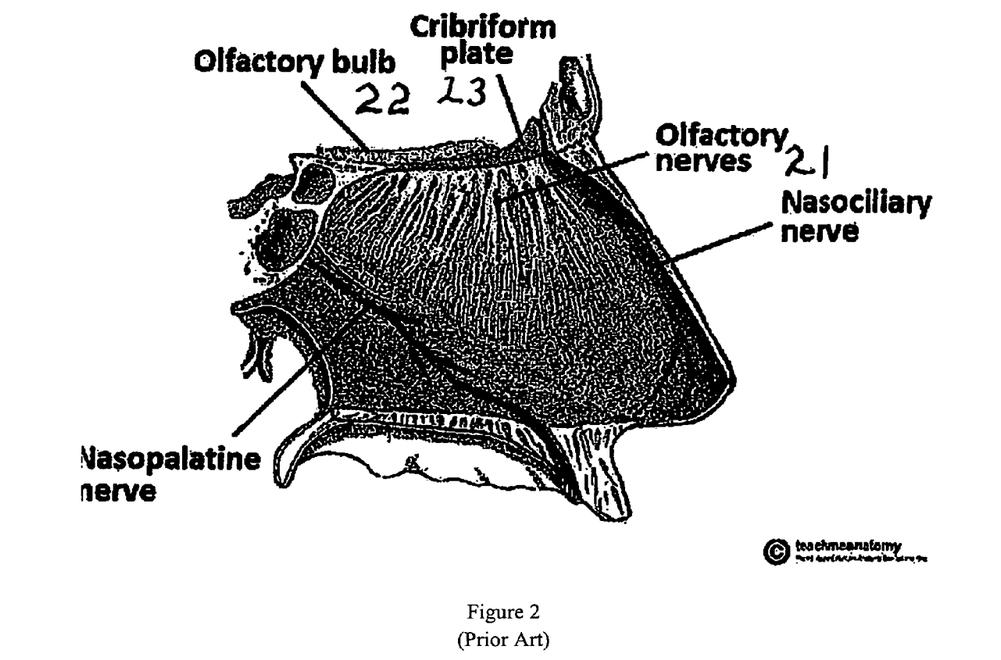
FIG. 2 illustrates additional anatomical elements of the nasal cavity.

Additional anatomical elements of the nasal cavity appear in FIG. 2. These anatomical elements include the olfactory nerves and the olfactory bulb indicated by the numerals 21 and 22, respectively. The olfactory bulb 22 is on the inferior (bottom) side of the brain.

In accordance with a non-limiting example of the present invention, the formulation is delivered slowly through the nares 1, 2 shown in FIG. 1 and infused into the inferior side of the brain of a patient suffering from traumatic brain injury by means of a delivery apparatus. A non-limiting example of the apparatus for delivering the formulation will now be described.

Figure 3:
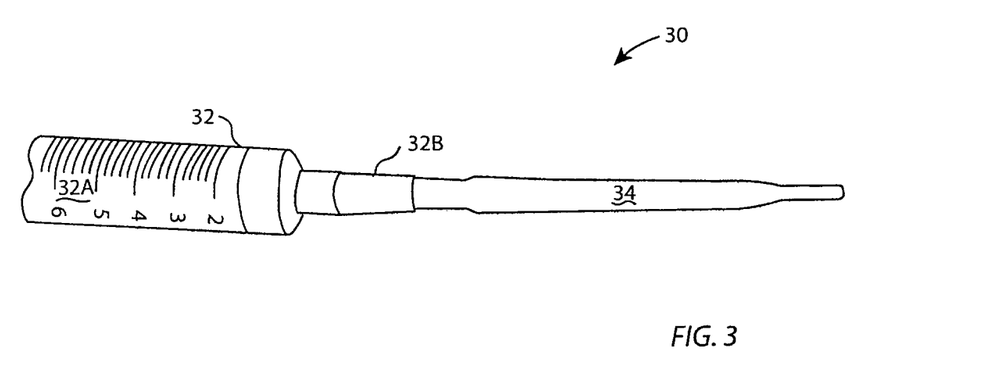
FIG. 3 is an elevational view of a nasal atomizer with a pipette extension for infusion of a formulation comprising platelet rich plasma infusion into a nostril(s) in accordance with an example embodiment of the present invention.

A non-limiting example of the formulation delivery apparatus in accordance with the present invention is shown in FIG. 3, generally indicated by the numeral 30. One non-limiting example of the delivery apparatus is a nasal atomizer comprising a 10 cc syringe 32 having a reservoir 32A and an atomizing dispensing tip 32B. The formulation delivery apparatus 30 further comprises a single-use pipette tip 34 selectively attached to the dispensing tip 32B of the syringe 32.

In order to administer the formulation to the patient suffering from traumatic brain injury, the pipette tip 34 is slid onto the dispensing tip 32B of the syringe 32. The reservoir of the syringe 32 is filled with 10 cc of the formulation described above.

The pipette tip 34 is then inserted into a naris 1, 2 of the traumatic brain injury patient, and the syringe 32 is actuated to provide a nasal atomizer with the pipette tip being positioned in the nasal cavity to provide delivery of the formulation to the fossa of the cribiform plate 23 shown in FIG. 2 under the nasal bridge just posterior to the frontal bone of the cranium to infuse the formulation into the patient's brain.

Figure 4:
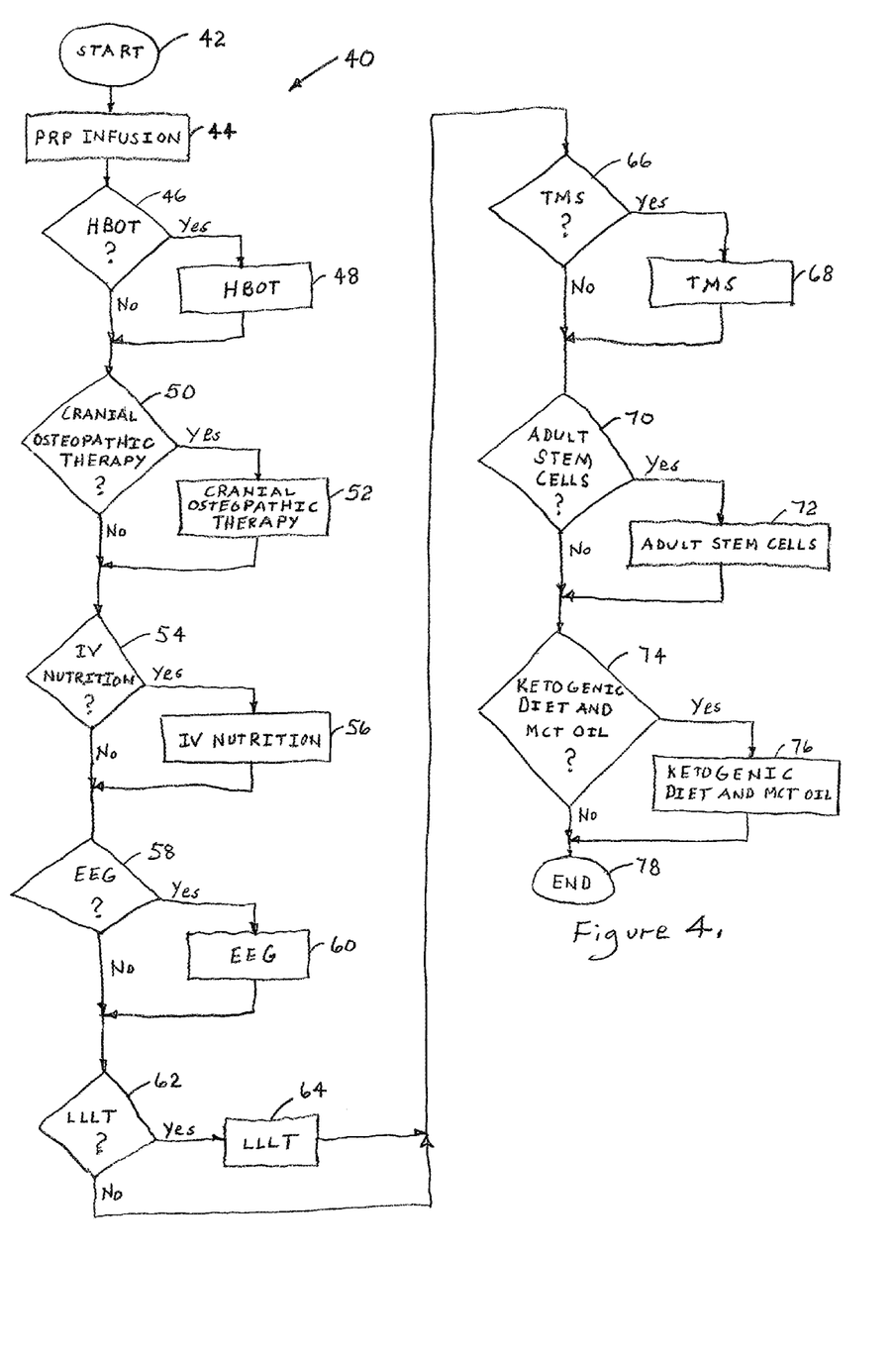
FIG. 4 is a flowchart of an example therapeutic treatment in accordance with an example embodiment of a method in accordance with the present invention.

A non-limiting example of a method in accordance with the present invention for treating a patient who has suffered traumatic brain injury, generally indicated by the numeral 40, is shown in FIG. 4. The treatment method commences with an initial consultation between a qualified physician and the patient, as indicated by a step 42. As indicated by a step 44, the patient is treated using PRP infusion consisting of the above-described formulation using the formulation delivery apparatus 30 at the time of the initial consultation. The step 44 is then repeated every three weeks for a total of three treatments over six weeks. Preferably, the PRP infusion therapy is then continued every four months for the following year.

In accordance with an additional non-limiting example of treatment method of the present invention, a regimen of one or more treatments using hyperbaric oxidation therapy (HBOT) is administered by the qualified physician to the patient who has experienced traumatic brain injury, as indicated by the "Yes" branch from a decision block 46. During the period of administration of the HBOT treatments, as indicated by a step 48, the patient is also treated using PRP infusion one or more times as described above. Additionally, following each treatment of PRP infusion, in accordance with a further non-limiting example of treatment method of the present invention, cranial osteopathic therapy is received by the patient, as indicated by the "Yes" branch from a decision block 50, and performed on the patient by the qualified physician, as indicated by a step 52.

In accordance with a further non-limiting example of the present invention, a regimen of 40 treatments using hyperbaric oxidation therapy (HBOT) at the step 48 is administered by a qualified physician to a patient, who has experienced brain trauma, over a period of six weeks. During the six-week period of administration of the HBOT treatments at the step 48, the patient is treated using PRP infusion at the step 44 at the time of the first HBOT treatment, at three weeks, and also at six weeks. Following each treatment using PRP infusion initially and again at three and six weeks, cranial osteopathic therapy at the step 52 is performed on the patient. By way of an additional non-limiting example of the treatment method in accordance with the present invention, cranial osteopathic therapy at the step 52 may be performed on the patient three days a week for the first six weeks, then two days a week for one month thereafter, and then one day a week for the remainder of the period of one year from the initial consultation.

In accordance with another non-limiting example of the present invention, a regimen of 40 initial treatments using hyperbaric oxidation therapy (HBOT) at the step 48 administered by a qualified physician to a patient, who has experienced brain trauma, over a period of six weeks is supplemented by two follow-up regimens of 20 treatments using HBOT at three and nine months from the initial HBOT regimen. The patient is treated using supplemental PRP infusions at the step 44 at four-month intervals for a year from the time that the initial HBOT treatment is administered at the step 48. Following each supplemental treatment using PRP infusion initially and again at four-month intervals for a year from the time that the initial HBOT treatment is administered at the step 48, cranial osteopathic therapy is performed on the patient at the step 52. By way of an additional non-limiting example of the treatment method in accordance with the present invention, cranial osteopathic therapy at the step 52 may be performed on the patient three days a week for the first six weeks, then two days a week for one month thereafter, and then one day a week for the remainder of the period of one year from the initial consultation.

In accordance with additional non-limiting examples of the present invention, PRP infusion, HBOT, and cranial osteopathic therapy may be further supplemented with additional therapies. The additional supplemental therapies may include one or more of the following therapies: intravenous (IV) nutrition, electroencephalographic (EEG) biofeedback, low level laser therapy (LLLT), transcranial magnetic stimulation (TMS), and adult stem cell treatments.

As shown in FIG. 4, in accordance with a further non-limiting example of the treatment method of the present invention, the patient receives IV nutrition therapy, as indicated by the "Yes" branch from a decision block 54, and performed on the patient by the qualified physician, as indicated by a step 56. IV nutrition therapy is recommended three times a week while the patient is receiving HBOT. The HBOT potentizes the nutrients used for the IV nutritional therapy so that the nutrients are made more bioavailable to the brain and other nervous system tissues.

As also shown in FIG. 4, in accordance with a still further non-limiting example of the treatment method of the present invention, the patient is trained using EEG biofeedback, as indicated by the "Yes" branch from a decision block 58, and performed on the patient, as indicated by a step 60. 40 initial EEG biofeedback treatments are recommended at the times that hyperbaric oxidation therapy (HBOT) is administered at the step 48 with 10 follow-up sessions of EEG biofeedback at the step 60 performed every two months for one year after the initial 40 sessions.

As additionally shown in FIG. 4, in accordance with yet a further non-limiting example of the treatment method of the present invention, the patient is treated using LLLT, as indicated by the "Yes" branch from a decision block 62, and performed on the patient, as indicated by a step 64. The LLLT therapy reduces inflammatory mediators such as prostaglandins, decreases bleeding, and improves mitochondrial ATP production. LLLT has been shown to penetrate the skull to directly aid damaged neurological tissue. LLLT therapy is performed daily for the first six weeks from the initial consultation at the step 42 and preferably immediately before or after HBOT is administered. Follow-up treatments using LLLT are also preferably performed again at the above-described three and nine month intervals at which HBOT is preferably administered totaling 60 treatments.

As further shown in FIG. 4, in accordance with another non-limiting example of the treatment method of the present invention, the patient may be treated using TMS therapy, as indicated by the "Yes" branch from a decision block 66, and performed on the patient, as indicated by a step 68. TMS therapy employs an electromagnetic field that causes depolarization of the neurons in the brain, which has been theorized to aid connections in the brain and improve the emotional aspects of the functioning of the human brain. Preferably, TMS therapy is performed daily for the first six weeks from the initial consultation at the step 42 and followed up with 20 additional sessions for a total of 50 treatments.

As also shown in FIG. 4, in accordance with a still further non-limiting example of the treatment method of the present invention, adult patients receive adult stem cell treatments, as indicated by the "Yes" branch from a decision block 70, and performed on the patient, as indicated by a step 72. These are stem cells harvested from the patient's fat, bone marrow, and blood plasma and infused by IV on the same day of the extraction. No cells are added, and only minimal manipulation is allowed per FDA guidelines. The procedure can be performed in approximately three hours and has proven to be very safe. Preferably, at least two adult stem cell treatments are recommended, for example, one treatment at the time of the initial consultation at the step 42 and a second treatment nine months later.

As further shown in FIG. 4, in accordance with another non-limiting example of the treatment method of the present invention, the patient may be treated using a ketogenic diet and medium-chain triglyceride (MCT) oil therapy, as indicated by the "Yes" branch from a decision block 74, as indicated by a step 76. The ketogenic diet and MCT oil produce an associated modification of the tricarboxylic acid cycle to increase the synthesis of the neurotransmitter gammaaminobutyric acid (GABA), leading to neuronal hyperpolarization and less of the neuroxcitatory glutamate. A ketogenic diet and MCT oil provide improved protection from oxidative stress and increased synthesis of calming neurotransmitters (including GABA). As shown in FIG. 4, the treatment method 40 concludes at a step 78.

The following is an example of a case study demonstrating the efficacy of treatment of a traumatic brain injury patient using the formulation described above infused using the formulation delivery apparatus 30.

The following case study chronicles a male patient with a traumatic brain injury (TBI) due to a serious motor vehicle accident in August 2012, during which he experienced a direct blow to the frontal region of the head and brain. This patient further experienced significant post-concussion symptoms secondary to the TBI, including insomnia, photosensitivity, hyperacusis, memory loss, decreased ability to concentrate, emotional distress, depression, loss of libido, daily headache pain, and loss of executive function, as well as other related symptoms.

It has been found that a protocol utilizing multiple modalities over a three-to-nine month period is an effective way to treat sub-acute and chronic traumatic brain injuries. This protocol is not limited to, but may include, hyperbaric oxygen therapy (HBOT), autologous human plasma, adult stem cells, and cranial osteopathic therapy along with the adjunctive therapies of EEG biofeedback, IV nutritional therapy, transcranial magnetic stimulation (TMS), and low-level light therapy. Although several modalities in the protocol have been utilized singularly, a combination of these therapies in a synergistic manner yields a novel approach towards the long-term remediation of TBI. Also, particularly unique to the protocol is the administration of activated plasma (in a solution of nutrients and drugs), as well as plasma-derived stem cells directly as a drip into the frontal area of the brain.

By way of background, on Aug. 28, 2012, the patient, who will hereafter be referred to as Mr. Chad, a 46-year-old male, was involved in a motor vehicle accident in which his automobile was struck at speed by another vehicle. Mr. Chad remembered his head hitting the visor and possibly the windshield before he felt a twisted snap and then "blacked out" and was taken to the emergency room. His right eye had "popped out" of its socket. Mr. Chad had left-sided numbness for a while with tingling into his left arm. He also experienced pain in his neck, left sacroiliac joint, and left lower extremity.

Mr. Chad had been evaluated by many specialists and therapists since the motor vehicle accident in August 2012. He reported gaining benefit from stem cell and plasma (as PRP) injections into the spinal region around his neck. Mr. Chad also reported a reduction in musculo-skeletal pain over time since the injury with use of a home HBOT chamber and intramuscular "stem-cell" injections at a clinic in Boulder, Colo. Mr. Chad reported that he had experienced some relief of symptoms in the late spring of 2013, with the daily use of a home hyperbaric oxygen chamber and five sessions of EEG biofeedback in Boulder, Colo. He also received an initial evaluation and treatment with neurology by a neuropsychologist of the Centeno-Schultz Clinic in Boulder, Colo. However, he continued to experience significant symptoms 11 months after the motor vehicle accident in August 2012.

Mr. Chad's primary concerns upon first presentation on Jul. 15, 2013 were the symptoms from his head injury. He reported extreme sound and light sensitivity, as well as an inability to do math or other focused exercises such as reading. Mr. Chad also reported bouts of depression, anxiety, and physical and mental fatigue. He reported memory loss, space and time recognition, loss of libido, inability to carry on conversations, as well as daily, continuous headaches. Mr. Chad also reported living in darkness, being able to only "withstand five seconds of sunlight."

At the time of intake, Mr. Chad denied current medications but reported using amino acids, 5 HTP, and a supplement known as Neuroreplete. He reported an allergic reaction to Codeine. His past medical history includes a tracheal cyst and stomach ulcer. Mr. Chad's family history is non-contributory. He denied the use of alcohol, tobacco, and drug abuse (with the exception of medical cannabis for headache pain). He lives alone in a warehouse.

Mr. Chad's review of his systems was significant for the following. He reported daily headaches. He reported trouble with temperature changes. He reported loss of peripheral vision that had improved since he started using the hyperbaric oxygen chamber at home. He reported seeing dark spots in his vision. He reported hyperacusis. He reported constant neck pain and stiffness. He reported indigestion and reflux. He reported pain in his lower back and sacroiliac area. He reported right knee pain secondary to hitting on the dashboard in the motor vehicle accident. He reported having no medial collateral ligament. He reported having trouble initiating words, actions; trouble following through with plans; trouble with concentration. He reported depression, anxiety, and insomnia.

At his physical examination on Jul. 15, 2013, Mr. Chad had stable vital signs and presented with no acute distress.

He was tender to palpation in the frontal area and temporal areas of his skull. He was wearing sunglasses and noise-canceling large headphones. He was able to hear in both ears. He had loss of vision peripherally, particularly significant in the right lower quadrant. His neck had a loss of range of motion, and he was most tender to palpation at the C5-C6 vertebral region bilaterally to the spine as well as C0 at the splenius capitus attachments. His lungs were clear to auscultation. His heart had a resting rate and regular rhythm with audible S1, S2 and no murmurs and no clicks. His abdomen was soft, with mild tenderness to palpation in the mid-epigastric area. He was mildly obese. His upper back was tender to palpation at the bilateral rhomboid attachments near vertebral region of T7-T8. He was tender to palpation at the left L5-S1 lumbro-sacral ligaments. He had tenderness to palpation at the left SI ligament. His upper extremity and lower extremity reflexes were intact and $\frac{2}{4}$ bilaterally. He had tenderness to palpation at the right medial knee. He had decreased grip strength of $\frac{3}{5}$ in his left hand. There were no obvious skin lesions. His affect was mildly depressed, but he expressed some hope based on his treatments using the hyperbaric oxygen chamber at home.

Mr. Chad's MRI study of his neck (dated Oct. 11, 2012) demonstrated a left-sided cervical disc extrusion at C5-6 on the left. Mr. Chad's MRI study of the brain with and without contrast (dated Oct. 11, 2012) was unremarkable for bleeding, mass, or appreciate insult to any area of the brain. Neither CT-scan nor PET/CT imaging studies had been performed on Mr. Chad.

Mr. Chad was still significantly mentally impaired when he presented on Jul. 15, 2013 in Basalt, Colo. At that time, Mr. Chad received an evaluation for commercialized HBOT therapy for TBI. Mr. Chad's plan was HBOT treatments at the standard TBI protocol of 1.5 atmospheres for 40 sessions. He was to undergo a neuropsychiatric evaluation to be completed in one week. He was to report about his sciatic pain and neck pain in two-to-three weeks. He was advised to take a baby aspirin daily and continue long-term follow-on treatment with neuropsychology, neurology, and physical therapy and to consider manual therapy to this head.

After an initial 25 sessions of HBOT at 1.5 atmospheres, cranial osteopathic therapy was performed on Mr. Chad, and activated plasma was administered to Mr. Chad in the form of injections, intravenous administration, and an intranasal drip. Mr. Chad also was given IV nutritional therapy to assist with his healing and recovery. He received 25 more HBOT treatments until the end of September 2013. The details of Mr. Chad's course of treatment are as follows.

From Jul. 15, 2013 to October 2013, Mr. Chad was treated with HBOT for 50 sessions at variable pressures ranging from 1.5 to 2.9 atmospheres. He received activated plasma injections on Aug. 26, 2013. He received activated plasma injections in the neck (composed of autologous human plasma, dextrose 5%, and calcium chloride ($\frac{1}{2}$ cc)) and activated plasma infusions (composed of autologous human plasma, dextrose 5%, 1 cc glutathione (200 mg/cc), $\frac{1}{2}$ cc methylcobalamin (5000 mcg/cc), 20 units of insulin, and 4 cc O3 at 12 ug/cc) intra-nasally via pipette to the cribriform fossa. Mr. Chad received IV nutritional therapy two times over the course of three months. He received cranial osteopathic therapy eight times over the course of 12 weeks. In October 2013, Mr. Chad received autologous adult stem cell treatments derived from the adipose tissue harvesting from his abdomen and bone marrow from his ilium.

Improvements on physical examination and neuropsychiatric testing formed the primary assessment tool for understanding Mr. Chad's condition and effectiveness of his treatment regimen. Physical examination findings in April 2014 (approximately nine months after treatment initiation in July 2013) include diminished light and sound sensitivity, decreased tenderness in affected musculo-skeletal areas, reduced fatigue, and calm affect. In October 2013, Mr. Chad also received adult stem cells derived from fat, plasma, and bone marrow in Miami, Fla.

From July 2013 to October 2013, Mr. Chad made significant, rapid improvements in cognition, executive function, emotional affect, insomnia, fatigue, fear, and pain along with having a decrease in light and sound sensitivity.

In October 2013, Mr. Chad was able to fly on an airplane to Miami, Fla. after only three months of treatment with HBOT, activated plasma, IV nutritional therapy, and cranial osteopathic therapy. In April 2014, six months after receiving adult stem cells, Mr. Chad demonstrated continued improvement and stabilization of his mental state. His neuropsychiatric evaluation also showed improvements. Third party follow-up post-treatment evaluations by a neuropsychologist in Boulder, Colo. also demonstrated improvements. Because Mr. Chad's traumatic brain injury was more neuropsychological than purely neurological, MRI and CT scans were not relied upon to determine significant effects of the protocol. It is noted that Mr. Chad had "fraying of his spinal cord" in the thoracic area as well as a cervical disc extrusion upon initial MRI but no major defects on MRI of the brain were observed upon initial presentation in July 2013. The assessment on Jul. 15, 2013 was moderate TBI with post-concussion syndrome with a wide neurological array of symptoms. He had cervical disc extrusion with possible radiculopathy into his left hand. He had sciatica, vision loss, and daily headaches.

From physical examination evidence and neuropsychiatric testing, Mr. Chad, a surviving TBI patient, made significant improvements in his mental capabilities and psychological response to the core treatment protocol involving HBOT, human plasma, cranial osteopathic therapy, and adult stem cells along with the adjunctive therapies of IV nutritional therapy and EEG biofeedback. Mr. Chad's results demonstrate improvements intellectually, physiologically, and psychologically along with mood and personality improvements. Improvements in Mr. Chad's brain condition and symptoms have been verified by an independent neuropsychologist in Boulder, Colo. Other patients with mild to moderate traumatic brain injuries have also benefited from a similar treatment protocol with reported findings of "a 37% increase in my Lumosity score, less crying, and more timed thoughts." Another mild-TBI patient who has completed a limited protocol reported that "my mind is more clear than it has been in years . . . . I am much closer to the vitality and clarity that I used to feel in my mind every day."

It is clear that Mr. Chad's case report demonstrates benefit of a treatment protocol with HBOT, human plasma, adult stem cells, and cranial osteopathic therapy (including the intranasal delivery of the autologous human plasma, nutrient, and insulin) for patients with mild to moderate traumatic brain injury. The utilization of EEG readings, PET scans, functional MRI scans, and more neuropsychological testing is warranted to further determine the full efficacy of the TBI treatment protocol.

While the foregoing description has been with reference to particular examples in accordance with the present invention, it will be appreciated by persons skilled in the art that changes in these examples may be made without departing from the principles and spirit of the invention. For example, the preferred parameters for the protocols in accordance with the various examples of the present invention described above are based on a sample of patients and may differ depending on the physical condition and characteristics of a given patient. Consequently, the parameters described for the various protocols are by way of example only and are to be considered to be within a range of the parameters that would apply to the general population as will be apparent to persons skilled in the art. Furthermore, in accordance with another non-limiting example of the present invention, a SphenoCath™ applicator available from Dolor Technologies, Inc. located in Salt Lake City, Utah may be used to infuse the formulations described above.

In addition to patients who have been treated for traumatic brain injury, patients whose brains have been injured with Reye's syndrome have also been successfully treated by the protocols in accordance with the various examples of the present invention described above. It is also believed that the protocols in accordance with the various examples of the present invention described above may be effective in the treatment of post-concussion syndrome (a mild, early form of brain injury) and chronic traumatic encephalopathy (CTE) and other later long-term consequences of untreated multiple brain injuries. Also, the administration of human PRP in accordance with the various examples of the present invention described above to treat stroke patients attenuates brain injury after focal ischemia following stroke. Furthermore, large, controlled studies, including level 1 evidence (which requires prospective examination and randomization), has led to a general acceptance that traumatic brain injury is a risk factor for developing Alzheimer's disease (AD). Accordingly, the protocols in accordance with the various examples of the present invention described above may be effective in reducing the incidence of AD. Accordingly, the scope of the present invention can only be ascertained with reference to the appended claims.

What is claimed is:

1. A method for treatment of patients who have experienced brain injury, comprising infusing a mixture of approximately 75% by volume human autologous plasma, 15% by volume D5W, 5% by volume glutathione, 4% by volume methylcobalamin, and less than 1% by volume regular insulin into the frontal region of the brain of a patient suffering from brain injury;
   wherein the mixture is infused using a nasal atomizer comprising a syringe and a single-use tip attached to the syringe; and
   wherein the tip is configured to be inserted into a naris of the brain injury patient, and the syringe is actuable to provide a nasal atomizer with the tip being positioned in the nasal cavity to provide delivery of the mixture to the fossa of the cribriform plate under the nasal bridge just posterior to the frontal bone of the cranium to infuse the mixture into the patient's brain.

2. A method as recited in claim 1 wherein the mixture is delivered directly adjacent to the brain through the nostrils or nares of the nasal cavity.

3. A method as recited in claim 1 wherein infusion of the mixture is repeated at three weeks and six weeks.

4. A method as recited in claim 3 wherein infusion of the mixture is repeated at four, eight, and 12 months.

5. A method as recited in claim 3, further comprising:
   administering to the patient a regimen of one or more treatments using hyperbaric oxidation therapy (HBOT); and
   performing cranial osteopathic therapy on the patient following each infusion of the mixture.

6. A method as recited in claim 5 wherein the regimen of treatments using hyperbaric oxidation therapy (HBOT) consists of 40 treatments administered to the patient over a period of six weeks.

7. A method as recited in claim 6, further comprising performing IV nutrition therapy on the patient three times a week while the patient is receiving the HBOT regimen.

8. A method as recited in claim 6, further comprising performing electroencephalographic (EEG) biofeedback training on the patient at the times that hyperbaric oxidation therapy (HBOT) is administered and performing additional sessions of EEG biofeedback training every two months for one year after the initial 40 sessions.

9. A method as recited in claim 6, further comprising treating the patient using LLLT therapy performed daily for the first six weeks immediately before or after HBOT is administered and at three and nine months daily for a week.

10. A method as recited in claim 3, further comprising performing cranial osteopathic therapy on the patient three days a week for the first six weeks, then two days a week for one month thereafter, and then one day a week for the remainder of the period of one year.

11. A method as recited in claim 1, further comprising performing intravenous (IV) nutrition therapy on the patient.

12. A method as recited in claim 1, further comprising performing EEG biofeedback training on the patient.

13. A method as recited in claim 1, further comprising treating the patient using low level laser therapy (LLLT).

14. A method as recited in claim 1, further comprising treating the patient using transcranial magnetic stimulation (TMS) therapy.

15. A method as recited in claim 14 wherein treating the patient using TMS therapy is performed daily for the first six weeks and followed up with 20 additional sessions for a total of 50 treatments.

16. A method as recited in claim 1, further comprising performing adult stem cell treatments on the patient.

17. A method as recited in claim 16 wherein one adult stem cell treatment is performed at the time of the infusion of the mixture and a second adult stem cell treatment is performed nine months later.

18. A method as recited in claim 1, further comprising administering to the patient a ketogenic diet and medium-chain triglyceride (MCT) oil therapy.

19. A method for treatment of patients who have experienced brain injury, comprising infusing a mixture of human autologous plasma, D5W, glutathione, methylcobalamin, and regular insulin into the frontal region of the brain of a patient suffering from brain injury;
   wherein the mixture consists of approximately 75% by volume human autologous plasma, 15% by volume D5W, 5% by volume glutathione, 4% by volume methylcobalamin, and less than 1% by volume regular insulin.

* * * * *